United States Patent
Fischer

(10) Patent No.: US 9,901,628 B2
(45) Date of Patent: Feb. 27, 2018

(54) HER2 DNA VACCINE AS ADJUNCT TREATMENT FOR CANCERS IN COMPANION ANIMALS

(71) Applicant: MERIAL INC., Duluth, GA (US)

(72) Inventor: Laurent Bernard Fischer, Sainte Foy les Lyon (FR)

(73) Assignee: MERIAL INC., Duluth, GA (US)

( * ) Notice: Subject to any disclaimer, the term of this patent is extended or adjusted under 35 U.S.C. 154(b) by 210 days.

(21) Appl. No.: 14/699,296

(22) Filed: Apr. 29, 2015

(65) Prior Publication Data

US 2015/0374808 A1    Dec. 31, 2015

Related U.S. Application Data

(63) Continuation of application No. 13/272,651, filed on Oct. 13, 2011, now Pat. No. 9,040,053.

(60) Provisional application No. 61/394,505, filed on Oct. 19, 2010.

(51) Int. Cl.
  *A61K 39/00* (2006.01)
  *A61K 48/00* (2006.01)

(52) U.S. Cl.
  CPC .......... *A61K 39/0011* (2013.01); *A61K 48/00* (2013.01); *A61K 2039/53* (2013.01); *A61K 2039/545* (2013.01)

(58) Field of Classification Search
  CPC ................................................ A61K 39/0011
  See application file for complete search history.

(56) References Cited

U.S. PATENT DOCUMENTS

2011/0142791 A1*  6/2011  Shahabi ............. A61K 39/0011
                                                                424/85.1

OTHER PUBLICATIONS

Peruzzi et al. (Vaccine. 2010; 28:1201-1208 [Available online Nov. 26, 2009]).*
Tu et al. (Vaccine. 2007; 25:719-728).*
Disis et al. (Immunology 1998; 93: 192-199).*
Gallo et al. (Int. J. Cancer. 2005: 113: 67-77).*
Bergman et al. (Cancer Therapy. 2008; 6: 817-826).*
Bachmeier et al. (International Journal of Oncology. 2008; 33: 1011-1015).*

* cited by examiner

*Primary Examiner* — Scott Long
(74) *Attorney, Agent, or Firm* — Judy Jarecki-Black; Chad Kitchen; Merial Inc.

(57) ABSTRACT

The application discloses therapeutic vaccines based upon the "pING" DNA plasmid vector expressing the gene encoding the rat Her2 protein. Vaccines according to the instant disclosure are used as an adjunct treatment for surgery, radiation and/or chemotherapy for dogs and cats with cancers that over express the Her2 antigen, and prolong the post-surgical disease free interval and/or survival time. Also included are therapeutically effective methods of immunization using said vaccines.

19 Claims, 7 Drawing Sheets

```
   1 ttggctattg gccattgcat acgttgtatc tatatcataa tatgtacatt
  51 tatattggct catgtccaat atgaccgcca tgttgacatt gattattgac
 101 tagttattaa tagtaatcaa ttacggggtc attagttcat agcccatata
 151 tggagttccg cgttacataa cttacgtaa atggcccgcc tggctgaccg
 201 cccaacgacc ccgcccatt gacgtcaatg atgacgtatg ttcccatagt
 251 aacgccaata gggactttcc attgacgtca atgggtggag tatttacggt
 301 aaactgccca cttggcagta catcaagtgt atcatatgcc aagtccgccc
 351 cctattgacg tcaatgacgg taaatggccc gcctggcatt atgcccagta
 401 catgacctta cgggactttc ctacttggca gtacatctac gtattagtca
 451 tcgctattac catggtgatg cggttttggc agtacaccaa tgggcgtgga
 501 tagcggtttg actcacgggg atttccaagt ctccacccca ttgacgtcaa
 551 tgggagtttg ttttggcacc aaaatcaacg ggactttcca aatgtcgta
 601 ataacccgc ccgttgacg caaatgggcg gtaggcgtgt acggtgggag
 651 gtctatataa gcagagctcg tttagtgaac cgtcagatcg cctggagacg
 701 ccatccacgc tgttttgacc tccatagaag acaccgggac cgatccagcc
 751 tccgcggccg gaacggtgc attggaacgc ggattccccg tgccaagagt
 801 gacgtaagta ccgcctatag actctatagg cacacccctt tggctcttat
 851 gcatgctata ctgttttgg cttggggcct atacaccccc gcttcttat
 901 gctataggtg atggtatagc ttagcctata ggtgtgggtt attgaccatt
 951 attgaccact cccctattgg tgacgatact ttccattact aatccataac
1001 atggctcttt gccacaacta tctctattgg ctatatgcca atactctgtc
1051 cttcagagac tgacacggac tctgtatttt tacaggatgg ggtcccattt
1101 attatttaca aattcacata tacaacaacg ccgtccccg tgcccgcagt
1151 ttttattaaa catagcgtgg gatctccacg cgaatctcgg gtacgtgttc
1201 cggacatggg ctcttctccg gtagcggcgg agcttccaca tccgagccct
1251 ggtcccatgc ctccagcggc tcatggtcgc tcggcagctc cttgctccta
1301 acagtggagg ccagacttag gcacagcaca atgcccacca ccaccagtgt
1351 gccgcacaag gccgtggcgg tagggtatgt gtctgaaaat gagctcggag
1401 attgggctcg caccgctgac gcagatggaa gacttaaggc agcggcagaa
1451 gaagatgcag gcagctgagt tgttgtattc tgataagagt cagaggtaac
1501 tcccgttgcg gtgctgttaa cggtggaggg cagtgtagtc tgagcagtac
1551 tcgttgctgc cgcgcgcgcc accagacata atagctgaca gactaacaga
                 NcoI (1611)   PstI (1624)
1601 ctgttcctt ccatgggtct tttctgcagt caccgtccac gcgttaatac
1651 gactcactat agggagaccc aagctggcta gcgtttaaac ttaagcttgg
                 BamHI (1711)            EcoRI (1734)
1701 taccgagctc ggatccacta gtccagtgtg gtggaattcc gggaaga
```

*FIG. 3*

```
3338 aaggcttagg caatagagta gggccaaaaa gcctgacctc actctaactc
3388 aaagtaatgt ccaggttccc agagaatatc tgctggtatt tttctgtaaa
3438 gaccatttgc aaaattgtaa cctaatacaa agtgtagcct tcttccaact
3488 caggtagaac acacctgtct ttgtcttgct gttttcactc agccctttta
3538 acattttccc ctaagcccat atgtctaagg aaaggatgct atttggtaat
3588 gaggaactgt tatttgtatg tgaattaaag tgctcttatt ttaaaaaacc
3638 ggaattctgc agatatccag cacagtggcg gccgctcgag tctagagggc
3688 ccgtttaaac ccgctgatca gcctcgactg tgccttctag ttgccagcca
3738 tctgttgttt gcccctcccc cgtgccttcc ttgaccctgg aaggtgccac
3788 tcccactgtc ctttcctaat aaaatgagga aattgcatcg cattgtctga
3838 gtaggtgtca ttctattctg ggggtgggg tgggcagga cagcaagggg
3888 gaggattggg aagacaatag caggcatggt ggggatgcag ggggggggg
3938 gcgctgaggt ctgcctcgtg aagaaggtgt tgctgactca taccaggcct
3988 gaatcgcccc atcatccagc cagaaagtga gggagccacg gttgatgaga
4038 gctttgttgt aggtggacca gttggtgatt ttgaactttt gctttgccac
4088 ggaacggtct gcgttgtcgg gaagatgcgt gatctgatcc ttcaactcag
4138 caaaagttcg atttattcaa caaagccgcc gtccgtcaa gtcagcgtaa
4188 tgctctgcca gtgttacaac caattaacca attctgatta gaaaaactca
4238 tcgagcatca aatgaaactg caatttattc atatcaggat tatcaatacc
4288 atatttttga aaaagccgtt tctgtaatga aggagaaaac tcaccgaggc
4338 agttccatag gatggcaaga tcctggtatc ggtctgcgat tccgactcgt
4388 ccaacatcaa tacaacctat taatttcccc tcgtcaaaaa taaggttatc
4438 aagtgagaaa tcaccatgag tgacgactga atccggtgag aatggcaaaa
4488 gcttatgcat ttctttccag acttgttcaa caggccagcc attacgctcg
4538 tcatcaaaat cactcgcatc aaccaaaccg ttattcattc gtgattgcgc
4588 ctgagcgaga cgaaatacgc gatcgctgtt aaaaggacaa ttacaaacag
4638 gaatcgaatg caaccggcgc aggaacactg ccagcgcatc aacaatattt
4688 tcacctgaat caggatattc ttctaatacc tggaatgctg ttttcccggg
4738 gatcgcagtg gtgagtaacc atgcatcatc aggagtacgg ataaaatgct
4788 tgatggtcgg aagaggcata aattccgtca gccagtttag tctgaccatc
4838 tcatctgtaa catcattggc aacgctacct ttgccatgtt tcagaaacaa
4888 ctctggcgca tcgggcttcc catacaatcg atagattgtc gcacctgatt
4938 gcccgacatt atcgcgagcc catttatacc catataaatc agcatccatg
                            XhoI (5006)
4988 ttggaattta atcgcggcct cgagcaagac gtttcccgtt gaatatggct
5038 cataacaccc cttgtattac tgtttatgta agcagacagt tttattgttc
5088 atgatgatat attttatct tgtgcaatgt aacatcagag attttgagac
                                    PstI (5162)
5138 acaacgtggc tttccccccc cccctgcag cgtttcttcc ttttccccac
```

FIG. 3 *(continued)*

```
5188  cccacccccc aagttcgggt gaaggcccag ggctcgcagc caacgtcggg
5238  gcggcaggcc ctgccatagc ctcaggttac tcatatatac tttagattga
5288  tttaaaactt cattttaat ttaaaaggat ctaggtgaag atccttttg
5338  ataatctcat gaccaaaatc ccttaacgtg agttttcgtt ccactgagcg
5388  tcagaccccg tagaaaagat caaaggatct tcttgagatc cttttttct
5438  gcgcgtaatc tgctgcttgc aaacaaaaaa accaccgcta ccagcggtgg
5488  tttgtttgcc ggatcaagag ctaccaactc ttttccgaa ggtaactggc
5538  ttcagcagag cgcagatacc aaatactgtt cttctagtgt agccgtagtt
5588  aggccaccac ttcaagaact ctgtagcacc gcctacatac ctcgctctgc
5638  taatcctgtt accagtggct gctgccagtg gcgataagtc gtgtcttacc
5688  gggttggact caagacgata gttaccggat aaggcgcagc ggtcgggctg
5738  aacgggggt tcgtgcacac agcccagctt ggagcgaacg acctacaccg
5788  aactgagata cctacagcgt gagctatgag aaagcgccac gcttcccgaa
5838  gggagaaagg cggacaggta tccggtaagc ggcagggtcg gaacaggaga
5888  gcgcacgagg gagcttccag ggggaaacgc ctggtatctt tatagtcctg
5938  tcgggtttcg ccacctctga cttgagcgtc gatttttgtg atgctcgtca
5988  gggggcgga gcctatggaa aaacgccagc aacgcggcct ttttacggtt
6038  cctggccttt tgctggcctt ttgctcacat gttcttcct gcgttatccc
6088  ctgattctgt ggataaccgt attaccgcca tgcattagtt attaatagta
6138  atcaattacg gggtcattag ttcatagccc atatatggag ttccgcgtta
                        BglI (6206)
6188  cataacttac ggtaaatggc ccgcctggct gaccgcccaa cgacccccgc
6238  ccattgacgt caataatgac gagatctgat ataggtgaca gacgatatga
6288  ggctatatcg ccgatagagg cgacatcaag ctggcacatg gccaatgcat
6338  atcgatctat acattgaatc aatattggca attagccata ttagtcattg
6388  gttatatagc ataaatcaat a
```

FIG. 3 (continued)

HER2 DNA VACCINE AS ADJUNCT TREATMENT FOR CANCERS IN COMPANION ANIMALS

CROSS-REFERENCE TO RELATED APPLICATIONS

This application is a continuation of, and claims priority to, U.S. application Ser. No. 13/272,651, filed on Oct. 13, 2011, which claims benefit of U.S. provisional application Ser. No. 61/394,505, filed Oct. 19, 2010.

BACKGROUND OF THE INVENTION

This application relates to compositions for treatment of differentiation antigen-dependent cancers and to methods of using such compositions. The invention utilizes compositions containing xenogeneic differentiation antigens, which are associated with cancers to provide effective therapy.

Differentiation antigens are tissue-specific antigens that are shared by autologous and some allogeneic tumors of similar derivation, and on normal tissue counterparts at the same stage of differentiation. Differentiation antigens have been shown to be expressed by a variety of tumor types, including melanoma, leukemia, lymphomas, colorectal carcinoma, breast carcinoma, prostate carcinoma, ovarian carcinoma, pancreas carcinomas, and lung cancers. For example, differentiation antigens expressed by melanoma cells include Melan-A/MART-1, Pmel17, tyrosinase, and gp75. Differentiation antigen expressed by lymphomas and leukemia include CD19 and CD20/CD20 B lymphocyte differentiation markers). An example of a differentiation antigen expressed by colorectal carcinoma, breast carcinoma, pancreas carcinoma, prostate carcinoma, ovarian carcinoma, and lung carcinoma is the mucin polypeptide muc-1. A differentiation antigen expressed by, for example, breast carcinoma is Her2 (synonyms: Her2/neu, ECBB2, ErbB2, c-erb-2), which is a gene coding for a tyrosine kinase receptor that is a member of the family of epidermal growth factor receptors (De Maria et al., 2005). Over expression of Her2 has been demonstrated in mammary gland tumors of both the cat (Winston et al., 2005) and the dog (Rungsipipat et al., 2008). Winston et al. (2005) used existing assay methods (HERCEPTEST™, Dako USA, Carpinteria, Calif.; NCL-CB11, Novocastra, Newcastle, UK) to successfully grade levels of Her2 expression on feline mammary tumors as 0=minimal/absent, 1=weak, 2=moderate, or 3=intense. The HERCEPTEST™ and NCL-CB11 assays identified 27 and 23 cats respectively, out of 30 examined, as having grade 2 or 3 Her2 expression in mammary tumor samples.

In addition to successfully grading levels of Her2 over expression in feline mammary tumors, Winston et al. (2005) used the HERCEPTEST™ to detect low levels of Her2 expression in normal feline epithelial tissues and cell types including: hair follicle, mammary gland, gastric pit, salivary gland duct, renal cortical and medullary tubules, colonic and small intestinal crypt, brain, pancreatic duct and islets, splenic macrophages, adrenal cortex, hepatocytes, and testicular Leydig's cells. Expression of Her2 has been documented on a range of human epithelial cell types including gastro-intestinal, respiratory, reproductive, urinary, skin, mammary and placenta (Press et al., 1990). These findings indicate that the expression of Her2 is common in a range of tissue types of humans and cats. The finding of Her2 over expression in dog mammary tumors suggests this species would share expression characteristics identified in humans and cats. Existing assays and reagents can serve as tools to screen expression levels of Her2 in companion animal cancers in order to justify treatment with the Her2 cancer vaccine.

Unfortunately, in most cases, the immune system of the individual is tolerant of such differentiation antigens, and fails to mount an effective immune response. Several technologies have been considered to address this challenge: (cytokines as genetic adjuvants (Chang et al., 2004), xenogeneic vaccination (Pupa et al., 2005), electrotransfer (Quaglino et al., 2004), combination with chemotherapy (Bernhardt et al., 2002). Although results were encouraging, greater efficacy was required for these approaches to be considered a key component of a first-line therapeutic strategy. Further, recent findings indicate both antibody and cell-mediated immunity are required for tumor eradication post immunization, perhaps explaining, in part, the lack of success in the field (Orlandi et al., 2007). Therefore, for the treatment of cancers where the tumor expresses differentiation antigens therefore, it would be desirable to have a method for stimulating a therapeutically effective immune response against the differentiation antigen in vivo. It an object of the present invention to provide such a method.

REFERENCES

Orlandi et al. Antibody and CD8[+] T cell Responses against HER2/neu Required for Tumor Eradication after DNA Immunization with a Flt-3 Ligand FusionVaccine. Clin Cancer Res 2007; 13(20) Oct. 15, 2007.

Amici A. et al. Venanzi F M, Concetti A. Genetic immunization against neu/erbB2 transgenic breast cancer. Cancer Immunol Immunother 1998; 47:183-90.

Bergman P J et al. Long-Term Survival of Dogs with Advanced Malignant Melanoma after DNA Vaccination with Xenogeneic Human Tyrosinase: A Phase I Trial. CCR, Vol. 9, 1284-1290, April 2003.

Bargmann et al. The neu oncogene encodes an epidermal growth factor receptor-related protein. Nature. 1986 Jan. 16-22; 319(6050):226-30.

Norell H et al. Vaccination with a plasmid DNA encoding HER2/neu together with low doses of GM-CSF and IL-2 in patients with metastatic breast carcinoma: a pilot clinical trial. JTM 7 Jun. 2010, 8:53.

Jacob, J B et al. Combining Human and Rat Sequences in Her2 DNA Vaccines Blunts Immune Tolerance and Drives Antitumor Immunity; Cancer Res Jan. 1, 2010 70; 119.

De Maria R et al. Spontaneous Feline Mammary Carcinoma is a Model of Her2 Overexpressing Poor Prognosis Human Breast Cancer; Cancer Res 2005: 65 (3); 907-912.

Philibert J C et al. Influence of Host Factors on Survival in Dogs with Malignant Mammary Gland Tumors; J Vet Intern Med 2003; 17:102-106.

Press M F et al. Expression of the Her2/neu proto-oncogene in normal human adult and fetal tissues; Oncogene, 5: 953-62.

Rungsipipat A et al.; C-erbB-2 oncogene and P21WAF/CIPI tumor suppressor gene expression as prognostic factors in canine mammary adenocarcinomas; Comp Clin Pathol 2008, 17:35-41.

Winston J et al. Immunohistochemical detection of Her=2/neu expression in spontaneous feline mammary tumours; Veterinary and Comparative Oncology 3, 1, 8-15, 2005.

Chang S Y et al. Enhanced efficacy of DNA vaccination against Her2/neu tumor antigen by genetic adjuvants; IJC vol 111 pages 86-95, 10 Aug. 2004

Pupa et al. HER2: A biomarker at the crossroads of breast cancer immunotherapy and molecular medicine. JCP Vol 205 pages 10-18, 10 May 2005.

Quaglino E et al. Concordant morphologic and gene expression data show that a vaccine halts HER2/neu preneoplastic lesions. JCI Vol 113 No 5 Mar. 2004

Bernhard H et al. Vaccination against the HER2/neu oncogenic protein. Endocrine-Related Cancer 9 (1) 33-44, 2002.

Berta, G N et al. Anti-HER2 DNA vaccine protects Syrian hamsters against squamous cell carcinomas. Br J Cancer, vol 93(11), 28 Nov. 2005.

Disis et al. Peptide-based, but not whole protein, vaccines elicit immunity to HER2/neu, an oncogenic self-protein. The Journal of Immunology 156: 3151-3158, May 1, 1996.

Eck et al. (Gene Based Therapy in The Pharmacological Basis of Therapeutics, Goodman and Gilman, Eds, 1996, pp. 77-101).

Zhai et al. Antigen-Specific Tumor Vaccines. The Journal of Immunology 156: 700-710, January 1996.

Verma and Somia. Gene and therapy-promises, problems and prospects. Nature 389: 239-242, September 1997.

Miller and Vile. Targeted vectors for gene therapy. FASEB J. 9: 190-199, 1995.

Deonarain, Mahendra. Ligand-targeted receptor-mediated vectors for gene delivery. Exp. Opin. Ther. Patents 8(1): 53-69, 1998.

Crystal. Transfer of Genes to Humans: Early Lessons and Obstacles to Success. Science 270: 404-410, Oct. 20, 1995.

B. Bouchard et al., "Induction of Pigmentation in Mouse Fibroblasts by Expression of Human Tyrosinase cDNA", J. Exp. Med., 1989, vol. 169, pp. 2029-2042.

B. Bouchard et al., "Production and Characterization of Antibodies against Human Tyrosinase", The Journal of Investigative Dermatology, 1994, vol. 102, No. 3, pp. 291-295.

J. Rowell et al., "Lysosome-Associated Membrane Protein-1-Mediated Targeting of the HIV-1 Envelope Protein to an Endosomal/Lysosomal Compartment Enhances Its Presentation to MHC Class II-Restricted T Cells", The American Association of Immunologists, 1995, pp. 1818-1828.

S. Krishnan et al., "Paving the way towards DNA vaccines", Nature Medicine, 1995, vol. 1, No. 6, pp. 521-522.

S. Barclay et al., "Rapid isolation of monoclonal antibodies specific for cell surface differentiation antigens", Proc. Natl. Acad. Sci. USA, 1986 vol. 83, pp. 4336-4340.

S. Vijayasaradhi et al., "Intracellular Sorting and Targeting of Melanosomal Membrane Proteins: Identification of Signals for Sorting of the Human Brown Locus Protein, GP75", The Journal of Cell Biology, 1995, vol. 130, No. 4, pp. 807-820.

D. Pardoll et al., "Exposing the Immunology of Naked DNA Vaccines", Immunity, Cell Press, 1995, vol. 3, pp. 165-169.

S. Vijayasaradhi et al., "The Melanoma Antigen gp75 is the Human Homologue of the Mouse b (Brown) Locus Gene Product", J. Exp. Med., 1990, vol. 171, pp. 1375-1380.

G. Adema et al., "Molecular Characterization of the Melanocyte Lineage-specific Antigen gp100", The Journal of Biology Chemistry, The American Society for Biochemistry and Molecular Biology, 1994, vol. 269, No. 31, pp. 20126-20133.

A. Houghton et al., "Recognition of Autoantigens by Patients with Melanoma", Annals New York Academy of Sciences, 1993, pp. 59-69.

C. Naftzger et al., "Immune response to a differentiation antigen induced by altered antigen: A study of tumor rejection and autoimmunity", Proc. Natl. Acad. Sci. USA, 1996, vol. 93, pp. 14809-14814.

F. Ausubel et al., "Expression of Proteins is Insect Cells using Baculoviral Vectors", Current Protocols in Molecular Biology, Greene Publishing and Wiley-Interscience, 1990, vol. 8, 16.8.1-16.11-7.

J. Ulmer et al., "Heterologous Protection Against Influenza by Injection of DNA Encoding a Viral Protein", Science, 1993, vol. 259, pp. 1745-1749.

C. Tiffs et al., "The Folding and Cell Surface Expression of CD4 Requires Glycosylation", The Journal of Biological Chemistry, 1992, vol. 267, No. 5, pp. 3268-3273.

S. Park, "J L1, A Novel Differentiation Antigen of Human Cortical Thymocyte", J. Exp. Med., The Rockefeller University Press, 1993, vol. 178, pp. 1447-1451.

C. Cabanas et al., "Characterization of a CD11c-Reactive Monoclonal Antibody (HCI/I) Obtained by Immunizing with Phorbol Ester Differentiated U937 Cells", Hybridoma, 1988, vol. 7, No. 2, pp. 167-177.

N. Nanda et al., "Induction of Anti-Self-Immunity to Cure Cancer", Cell, 1995, vol. 82, pp. 13-17. cited by other.

All of the above-mentioned applications, patents and references are herein incorporated in their entirety by reference.

SUMMARY OF THE INVENTION

It has now been found that the tolerance of the immune system for self-derived target differentiation antigens can be overcome and an immune response stimulated by administration of a xenogeneic differentiation antigen (wild-type or mutant) of the same type from a species different from the subject being treated (U.S. Pat. No. 6,328,969 & U.S. Pat. No. 7,556,805, to Sloan-Kettering, both incorporated by reference herein). For example, a rat differentiation antigen can be used to stimulate an immune response to the corresponding differentiation antigen in a canine subject. Administration of altered antigens in accordance with the invention results in an effective immunity against the original antigen expressed by the cancer in the treated subject. Thus, in accordance with a first aspect of the invention, there is provided a method for treating in a mammalian subject, comprising the step of administering to the subject an immunologically-effective amount of a xenogeneic mammary gland tumor-associated differentiation antigen.

Therapeutic differentiation antigens based on mammary gland carcinoma/tumor-associated differentiation antigens are used in accordance with the invention to treat, for example, mammary gland carcinoma post-surgical removal of tumors in subjects suffering from said cancers. In one embodiment of the invention, a plasmid comprising a sequence encoding a xenogeneic tyrosine kinase receptor, for example rat tyrosine kinase receptor, under the control of a suitable promoter, is administered to a subject. For example, dogs have been treated using plasmids comprising a DNA sequence encoding rat tyrosine kinase receptor with pronounced clinical benefit.

BRIEF DESCRIPTION OF THE DRAWINGS

FIG. 3 shows a sequence for the pINGhumanTyrosinase plasmid, where the coding sequence for the human tyrosinase has been removed. This is where the rat Her2/neu (nucleotides 17-3799 of SEQ ID NO:1) was inserted to produce rHer2/neu-pING of the instant invention;

DETAILED DESCRIPTION OF THE INVENTION

Figure 1A:
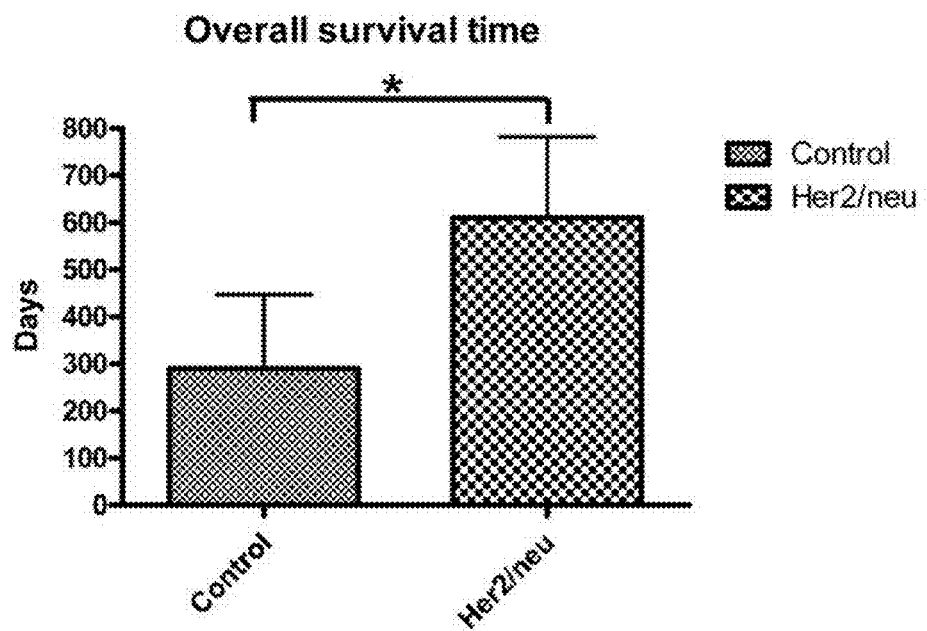
FIG. 1A shows overall survival time post-immunization and surgical resection of MGT.

The present invention provides a method for treating mammary gland tumors in a subject by stimulating an immune response to a mammary gland-associated differentiation antigen. The subject is preferably canine or feline, although the invention can be applied to other animal species, preferably mammalian or avian species, as well.

As used in the specification and claims of this application, the term "immune response" encompasses both cellular and humoral immune responses. Preferably, the immune response is sufficient to provide immunoprotection against growth of tumors expressing the target differentiation antigen. The term "stimulate" refers to the initial stimulation of a new immune response or to the enhancement of a pre-existing immune response.

In accordance with the invention, a subject is treated by administering a xenogeneic differentiation antigen of the same type as a target differentiation antigen expressed by mammary gland tumor cells of the subject in an amount effective to stimulate an immune response. Thus, for example, if the target differentiation antigen is the Her2/neu antigen found in mammary cells, the therapeutic antigen is a xenogeneic Her2/neu antigen.

In one embodiment, the inventive method may include the following steps: (1) immunization to an animal in need of a xenogeneic antigen, for example, the rat Her2/neu as set forth in SEQ ID NO:2 and encoded by nucleotides 106-3885 of the sequence as set forth in SEQ ID NO:1, (2) needle-free priming of immune responses, (3) electrotransfer-based booster, and (4) vaccination after tumor debulking by surgical primary therapy.

In another embodiment, the inventive method is carried out on subjects, including companion animals, without metastasis (i.e. in relatively early stages of mammary carcinoma disease progression).

In some embodiments, the boost comprises administering plasmids encoding xenogeneic antigens, for example those encoding rat Her2 protein (SEQ ID NO:2).

In some embodiments, the xenogeneic antigen is encoded by a nucleotide having favorable nucleotide substitutions with respect to the sequence as set forth in SEQ ID NO:1. Favorable substitutions include any changes that result in improved immune response against the Her2/neu expressed by the cells of the mammary tumor/carcinoma. Substitutions can include existing sequences, such as murine Her2 (SEQ ID NO:3), human Her2 (SEQ ID NO:4), or any other xenogeneic Her2 sequence, or fragment thereof, capable of eliciting a therapeutically effective immune response in a target animal against a Her2-associated mammary carcinoma.

In some embodiments, the boost comprises administering a xenogeneic differentiation antigen.

In other embodiments, the boost comprises administering a syngeneic differentiation antigen.

Xenogeneic differentiation antigen may be administered as a purified differentiation antigen derived from the source organism. Proteins can be purified for this purpose from cell lysates using column chromatography procedures. Proteins for this purpose may also be purified from recombinant sources, such as bacterial or yeast clones or mammalian or insect cell lines expressing the desired product.

Administration of the xenogeneic differentiation antigen can be accomplished by several routes. First, the xenogeneic differentiation antigen may be administered as part of a vaccine composition which may include one or more adjuvants such as alum, QS21, TITERMAX or its derivatives, incomplete or complete Freund's and related adjuvants, and cytokines such as granulocyte-macrophage colony stimulating factor, flt-3 ligand, interleukin-2, interleukin-4 and interleukin-12 for increasing the intensity of the immune response. The vaccine composition may be in the form of a xenogeneic differentiation antigen in a solution or a suspension, or the therapeutic differentiation antigen may be introduced in a lipid carrier such as a liposome. Such compositions will generally be administered by subcutaneous, intradermal or intramuscular route. Vaccine compositions containing expressed xenogeneic differentiation antigen are administered in amounts which are effective to stimulate an immune response to the target differentiation antigen in the subject. The preferred amount to be administered will depend on the species of the subject and on the specific antigen, but can be determined through routine preliminary tests in which increasing doses are given and the extent of antibody formation or T cell response is measured by ELISA or similar tests. T cell responses may also be measured by cellular immune assays, such as cytotoxicity, cytokine release assays and proliferation assays.

The xenogeneic differentiation antigen may also be introduced in accordance with the invention using a DNA immunization technique in which DNA encoding the antigen is introduced into the subject such that the xenogeneic differentiation antigen is expressed by the subject. cDNA encoding the differentiation antigen is combined with a promoter which is effective for expression of the nucleic acid polymer in mammalian cells. This can be accomplished by digesting the nucleic acid polymer with a restriction endonuclease and cloning into a plasmid containing a promoter such as the SV40 promoter, the cytomegalovirus (CMV) promoter or the Rous sarcoma virus (RSV) promoter. The resulting construct is then used as a vaccine for genetic immunization. The nucleic acid polymer could also be cloned into plasmid and viral vectors that are known to transduce mammalian cells. These vectors include retroviral vectors, adenovirus vectors, vaccinia virus vectors, pox virus vectors and adenovirus-associated vectors.

The nucleic acid constructs containing the promoter and the antigen-coding region can be administered directly or they can be packaged in liposomes or coated onto colloidal gold particles prior to administration. Techniques for packaging DNA vaccines into liposomes are known in the art, for example from Murray, ed. "Gene Transfer and Expression Protocols" Humana Pres, Clifton, N.J. (1991). Similarly, techniques for coating naked DNA onto gold particles are taught in Yang, "Gene transfer into mammalian somatic cells in vivo", Crit. Rev. Biotech. 12: 335-356 (1992), and techniques for expression of proteins using viral vectors are found in Adolph, K. ed. "Viral Genome Methods" CRC Press, Florida (1996).

For genetic immunization, the vaccine compositions are preferably administered intradermally, subcutaneously or intramuscularly by injection or by gas driven particle bombardment, and are delivered in an amount effective to stimulate an immune response in the host organism. The compositions may also be administered ex vivo to blood or bone marrow-derived cells (which include APCs) using liposomal transfection, particle bombardment or viral infection (including co-cultivation techniques). The treated cells are then reintroduced back into the subject to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, starting at about 0.1 µg is administered and the resulting immune response is observed, for example by measuring antibody titer using an ELISA assay, detecting CTL response using a chromium release assay or detecting TH (helper T cell) response using a cytokine release assay.

Once tolerance is broken through the administration of the xenogeneic differentiation antigen, subsequent treatments with syngeneic differentiation may be employed to maintain and in some cases enhance the immune response. (See, Weber, et al., "Tumor immunity and autoimmunity induced by immunization with homologous DNA." J Clin Invest 102 (6):1258 (1998).) Thus, in one embodiment of the invention, the subject is first treated by administration of a xenogeneic differentiation antigen (for example for three treatment cycles), and subsequently by administration of a syngeneic differentiation antigen (for example for an additional three treatment cycles). As an alternative to treatment cycles using different therapeutic agents, one can use a single therapeutic agent containing both xenogeneic and syngeneic differentiation antigens. Thus, for example, a mixture of the rHer2-pING and hHer2-pING vectors, or a single vector encoding both rat and human Her2/neu under the control of a promoter such that they are expressed in a canine subject can be employed for the treatment of mammary gland tumor in canines. Vectors are available commercially, for example from Stratagene and other companies, which can express two independent genes. Commonly, these vectors use an internal ribosomal entry site, or IRES, between the two genes. This approach has the advantage of requiring approval for only a single therapeutic agent.

All documents cited herein are herein incorporated by reference in their entirety.

The invention will now be further described with reference to the following, non-limiting examples.

Example 1—Her2/neu Expression Plasmid Construction

Figure 2:
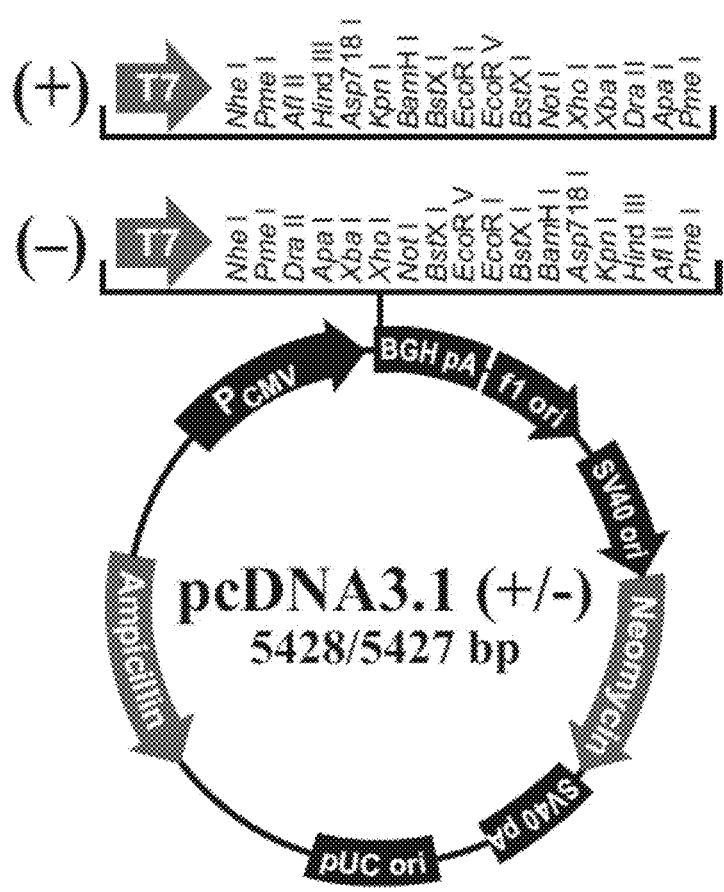
FIG. 2 shows a map of the pcDNA3.1 (+/−) plasmid
Figure 4:
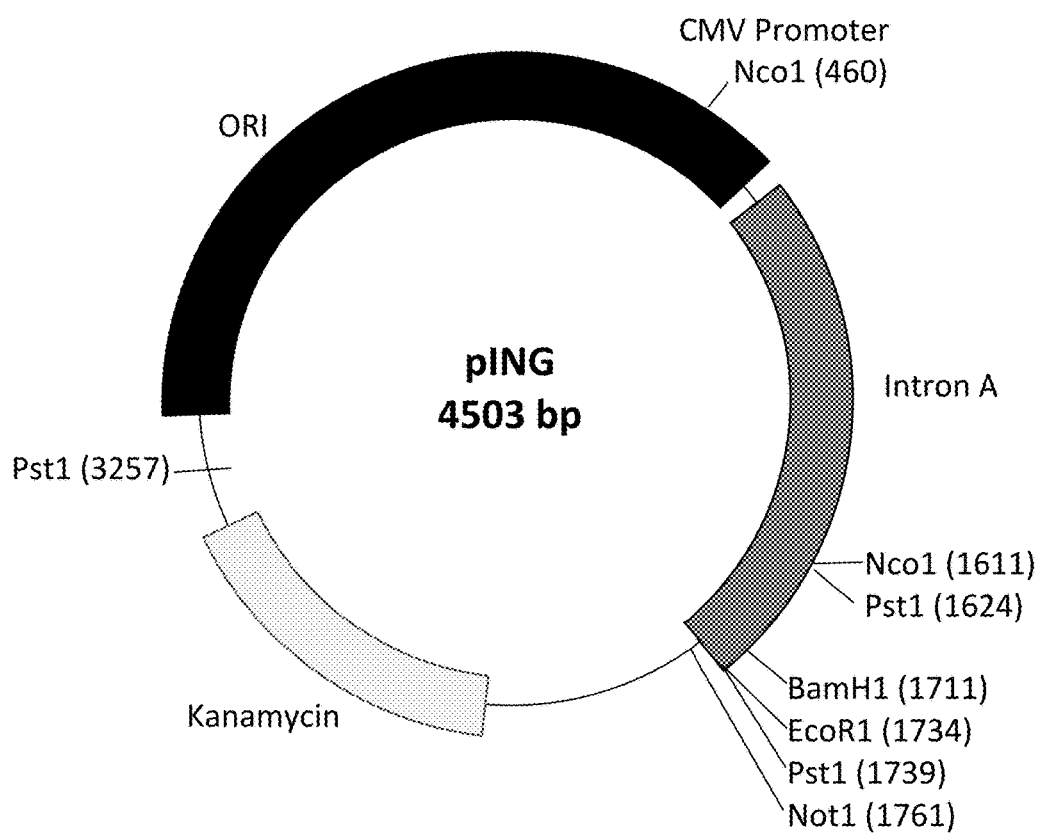
FIG. 4 shows a map of the pING plasmid.

The extracellular domain of rat HER2/neu (nucleotides 17-3799 of SEQ ID NO:1) was amplified by PCR from the pCMVneuNT (Amici et al., 1998) plasmid using the primers forward: 5'-CGAAGCTTACCATGGAGCTGGCGGC-CTGG-3' (SEQ ID NO:6) and reverse: 5'-CGGAATTCT-TATGTCACCGGGCTGGC-3' (SEQ ID NO:7). The HindIII-EcoRI fragment was cloned into pcDNA3.1(+) (Invitrogen, Carlsbad, Calif.; and FIG. 2). The original sequence of the rat neu cDNA was described previously (Bargmann et al., 1986), and is herein set forth in SEQ ID NO:1, with the coding sequence from nucleotides 17 to 3799. The rat HER2/neu coding sequence was then subcloned into the pING vector (Bergman et al., Clin Cancer Res, 9: 1284-1290, 2003, backbone depicted in FIG. 3; map depicted in FIG. 3A; and sequence as set forth in SEQ ID NO:5), to yield rat HER2/neu-pING.

Example 2—Immunization of Mammary Gland Tumor (MGT)-Positive Canines with pING-rHer2

In this trial, 10 dogs with MGT were enrolled and immunized with 100 µg of pING-rHer2 DNA per dose. The signalment for these dogs is set forth in Table 1 and the tumor staging is set forth in Table 2.

TABLE 1

Trial animal characteristics

|  | Age (yrs) | Breed | Weight (kg) |
| --- | --- | --- | --- |
| MGT 01 | 9 | Yorkshire Terrier | 1.75 |
| MGT 02 | 13 | Mixed | 9.8 |
| MGT 03 | 12 | Yorkshire Terrier | 5 |
| MGT 04 | 7 | Lhasa Apso | 11 |
| MGT 05 | 10 | Maltese | 3.35 |
| MGT 06 | 12 | Cavalier King Charles Spaniel | 9 |
| MGT 07 | 8 | Pomeranian | 2.8 |
| MGT08 | 12 | Maltese | 3.9 |
| MGT09 | 13 | Pomeranian | 2.7 |
| MGT10 | 12 | Yorkshire Terrier | 3 |
| Median | 12 | — | 3.6 |

TABLE 2

Tumor staging

|  | Tumor size (cm) | MGT Type | Stage |
| --- | --- | --- | --- |
| MGT 01 | 2 × 2 × 4<br>0.2 × 0.2 × 0.2<br>0.2 × 0.3 × 0.2<br>0.1 × 0.1 × 0.1<br>0.5 × 0.5 × 0.5<br>0.2 × 0.2 × 0.2<br>0.5 × 0.5 × 0.5 | Tubulopapillary carcinoma | $T_3N_0M_0$ |
| MGT 02 | 12 × 10 × 8<br>5 × 3 × 1.5<br>1 × 1 × 1<br>1 × 1 × 0.5<br>0.5 × 0.1 × 0.1 | Lipid rich carcinoma | $T_3N_0M_0$ |
| MGT 03 | 5.6 × 4.8 × 4.6<br>1.8 × 1.5 × 1.2 | Tubulopapillary carcinoma with fibroadenoma | $T_3N_0M_0$ |
| MGT 04 | 4.2 × 5.6 × 2.5 | Tubulopapillary carcinoma | $T_3N_0M_0$ |
| MGT 05 | 1.2 × 1 × 0.5<br>1 × 1.4 × 0.5<br>1 × 1 × 0.4<br>0.5 × 0.5 × 0.5 | Simple adenoma | $T_1N_0M_0$ |
| MGT 06 | 10 × 4 × 3 | Lipid rich carcinoma with fibroadenoma | $T_3N_0M_0$ |
| MGT 07 | 1 × 1 × 1<br>0.5 × 0.5 × 0.5 | Complex type | $T_1N_0M_0$ |
| MGT08 | 1 × 1 × 1<br>0.5 × 0.5 × 0.5 | Complex type | $T_1N_0M_0$ |
| MGT09 | 2.5 × 2 × 1<br>1.5 × 2 × 1 | Complex type | $T_1N_0M_0$ |
| MGT10 | 1 × 1 × 1<br>0.5 × 0.5 × 0.5<br>0.1 × 0.1 × 0.1 | Tubulopapillary carcinoma | $T_1N_0M_0$ |

As indicated, this group included five stage I and five stage III dogs, which all received three doses of vaccine at two week intervals. The first and second doses were administered with the VITAJET™ transdermal device and the third dose by intramuscular injection concurrent with electroporation. Vaccination was initiated following surgical removal of the MGT with concurrent ovariohysterectomy (OHE). All dogs were negative for regional lymph node and pulmonary metastasis. Disease free survival and overall survival times were calculated using day of surgery as day 0 with results presented in Table 3.

TABLE 3

Disease-free and overall survival time

| Dog | WHO Stage | Disease-free survival recurrence | metastasis | Overall survival time (days) | Outcome |
|---|---|---|---|---|---|
| MGT 05 | I | 703 | 703 | 703 | alive |
| MGT 07 | I | 669 | 669 | 669 | alive |
| MGT 08 | I | 548 | 548 | 548 | alive |
| MGT 09 | I | 536 | 536 | 536 | alive |
| MGT 10 | I | 482 | 482 | 482 | dead |
| Stage I Dogs | | 548 | 548 | 548 | — |
| MGT 01 | III | 779 | 779 | 779 | alive |
| MGT 02 | III | 212 | 182 | 212 | dead |
| MGT 03 | III | 762 | 762 | 762 | alive |
| MGT 04 | III | 575 | 381 | 720 | alive w/ met |
| MGT 06 | III | 686 | 686 | 686 | alive |
| Stage III Dogs | | 686 | 686 | 720 | — |
| All Dogs Median | | 622 | 609 | 678 | |

Figure 1B:
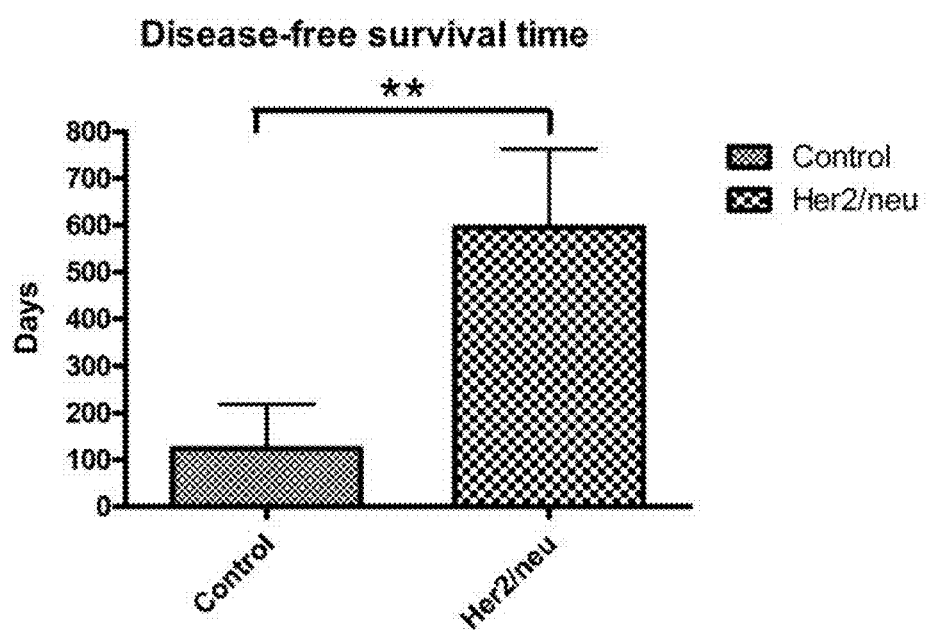
FIG. 1B shows disease-free survival time post-immunization and surgical resection of MGT.
Figure 1C:
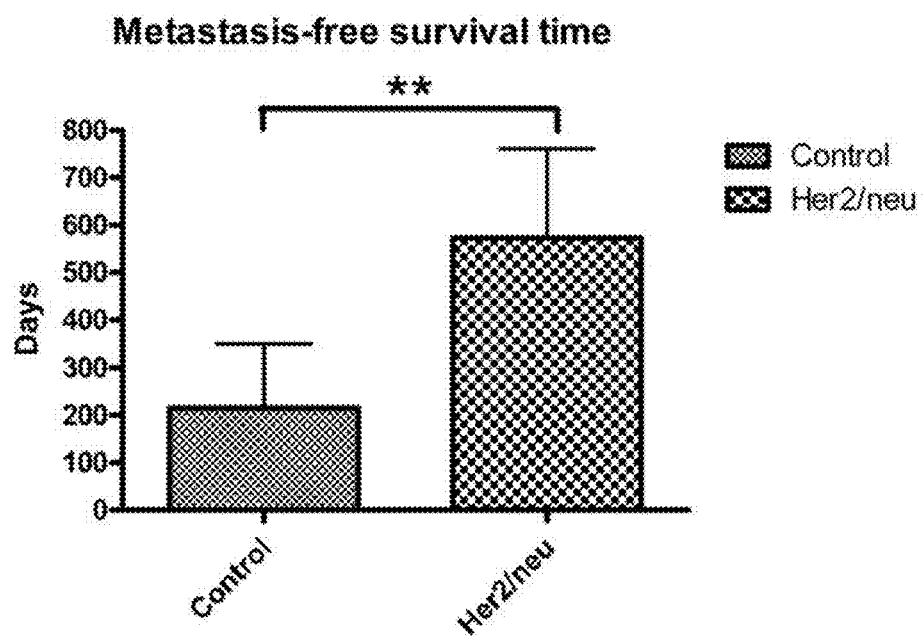
FIG. 1C shows metastasis-free survival time post-immunization and surgical resection of MGT.

A group of 19 dogs was identified as historical control cases. All control dogs underwent surgical removal of MGT with concurrent OHE and were negative for regional lymph node and pulmonary metastasis. This group included 7 stage I, 3 stage II, and 9 stage III dogs. Disease free and overall survival times were calculated for these dogs using day of surgery as day 0. The signalment for these dogs is set forth in Table 4 and tumor staging for each dog is set forth in Table 5. Disease free and overall survival times were calculated for the control group and are presented in FIGS. 1A-1C.

TABLE 4

Control dog signalment

| | Case Number | Age (yrs) | Breed | Weight (kg) |
|---|---|---|---|---|
| 1 | 9403460 | 7 | Mix | 1.75 |
| 2 | 9404023 | 14 | Poodle | 2.5 |
| 3 | 9405132 | 14 | Yorkshire | 2.3 |
| 4 | 9409179 | 12 | Finnish Spitz | 6.8 |
| 5 | 9409043 | 14 | Poodle | 3.2 |
| 6 | 9500057 | 9 | Lhasa Apso | 6.5 |
| 7 | 9500890 | 14 | Maltese | 6 |
| 8 | 9500959 | 15 | Cocker | 14 |
| 9 | 923543 | 11 | Siberian Huskies | 16 |
| 10 | 9405082 | 13 | Poodle | 3.9 |
| 11 | 9505202 | 9 | Mix | 12 |
| 12 | 9600998 | 10 | Maltese | 4.6 |
| 13 | 9700451 | 13 | Maltese | 2.7 |
| 14 | 892285 | 12 | Yorkshire | 1.6 |
| 15 | 9502927 | 14 | Maltese | 3.2 |
| 16 | 9405356 | 10 | Cocker | 12 |
| 17 | 9409104 | 11 | Maltese | 3.8 |
| 18 | 9503957 | 6 | Miniature Schnauzer | 4 |
| 19 | 9404023 | 14 | Poodle | 3 |
| | Median | 12 | | 3.9 |

TABLE 5

Tumor staging for control dogs

| | Clinical NO. | Tumor size | MGT Type | Stage |
|---|---|---|---|---|
| 1 | 9403460 | 6 × 6 × 7 | Complex carcinoma | $T_3N_0M_0$ |
| 2 | 9404023 | 3 × 3 × 3 | Squamous cell carcinoma | $T_2N_0M_0$ |
| 3 | 9405132 | 7 × 4 × 7<br>2 × 2 × 2<br>0.3 × 0.2 × 0.2<br>0.5 × 0.5 × 0.5 | Simple or complex carcinoma | $T_3N_0M_0$ |
| 4 | 9409179 | 13 × 12 × 12<br>6 × 7 × 7<br>1 × 1 × 1 | Simple carcinoma with squamous cell carcinoma | $T_3N_0M_0$ |
| 5 | 9409043 | 3.5 × 2.x1<br>3 × 1.5 × 1 | Tubulopapillary carcinoma | $T_2N_0M_0$ |
| 6 | 9500057 | 3 × 2 × 2<br>2 × 1 × 1 | Tubulopapillary carcinoma | $T_2N_0M_0$ |
| 7 | 9500890 | 8 × 3 × 1 | Simple carcinoma | $T_3N_0M_0$ |
| 8 | 9500959 | 8 × 3 × 2<br>2 × 1 × 0.5 | Adenocarcinoma | $T_3N_0M_0$ |
| 9 | 923543 | 5 × 5 × 4<br>0.2 × 0.2 × 0.2 | Simple carcinoma | $T_3N_0M_0$ |
| 10 | 9405082 | 5 × 4 × 3.5<br>3 × 3.5 × 3 | Simple carcinoma | $T_3N_0M_0$ |
| 11 | 9505202 | 0.3 × 0.3 × 0.3<br>1 × 1 × 0.5<br>0.4 × 0.4 × 0.4 | Tubulopapillary carcinoma | $T_1N_0M_0$ |
| 12 | 9600998 | 0.5 × 0.5 × 0.4<br>1 × 0.5 × 0.5 | Carcinoma | $T_1N_0M_0$ |
| 13 | 9700451 | 1 × 1 × 1<br>1 × 1 × 1 | Tubulopapillary carcinoma | $T_1N_0M_0$ |
| 14 | 892285 | 0.5 × 0.8 × 0.3<br>1 × 0.8 × 0.5 | Carcinoma in benign mixed tumor | $T_1N_0M_0$ |
| 15 | 9502927 | 5 × 4 × 4<br>0.5 × 0.5 × 0.5 | Carcinoma in benign mixed tumor | $T_3N_0M_0$ |
| 16 | 9405356 | 10 × 3 × 1.5 | Tubulopapillary carcinoma | $T_3N_0M_0$ |
| 17 | 9409104 | 1 × 1 × 1<br>0.5 × 0.5 × 0.5<br>2 × 2 × 2 | Adenocarcinoma | $T_1N_0M_0$ |
| 18 | 9503957 | 2 × 2 × 2<br>0.3 × 0.3 × 0.3 | Adenocarcinoma, complex type | $T_1N_0M_0$ |
| 19 | 9404023 | 2 × 2 × 1 | Adenocarcinoma, | $T_1N_0M_0$ |

Philibert et al. (2003) reviewed survival statistics for 97 dogs with MGT and reported median survival times for 41 dogs with MGT less than 3 cm in diameter to be 22 months (~666 days) versus 14 months (~424 days) for 56 dogs with MGT greater than 3 cm in diameter. In the absence of lymph node involvement or metastasis, tumor size less than 3 cm correlates with stage I disease and greater than 3 cm correlates with stage II or higher disease status. They did not find a difference in survival time for dogs in stages II, III or IV.

Overall median survival time for all dogs treated with the pING-rHer2 vaccine is 678 days. This was significantly higher as compared to the historical data from the 19 dogs provided by NTU indicating a median overall survival time of 300 days, and to the data published by Philibert et al. (2003) indicating 424 days overall survival time for dogs with stage II or greater MGT.

The pING-rHer2 DNA vaccine will target dogs and cats with tumors shown to over express the Her2 antigen based upon tumor tissue analysis using existing Her2 tissue expression assays. The vaccine will be administered using the Vetjet™ transdermal device to deliver 100 µg of DNA into the medial thigh of dogs or lateral thigh of cats, at two week intervals for four doses. Dogs and cats that survive will receive a booster dose every six months.

The invention will now be described by the following non-limiting claims.

What is claimed is:

1. A method for treating canine mammary carcinoma/tumor in a dog suffering from a canine mammary carcinoma/tumor comprising cells expressing a xenogeneic mammary gland-associated differentiation antigen, comprising:
    a) surgically debulking the mammary carcinoma/tumor; and
    b) administering to said dog a clinically-effective amount of a first nucleic acid molecule comprising a DNA sequence encoding a xenogeneic mammary gland-associated differentiation antigen under the control of a promoter which promotes expression of said xenogeneic mammary gland-associated differentiation antigen in said dog; and
    wherein canines receiving said nucleic acid molecule exhibit significantly increased overall, disease-free, and/or metastasis-free survival times relative to canines receiving the surgical debulking without subsequent administration of said nucleic acid molecule, thereby treating said carcinoma/tumor.

2. The method of claim 1, wherein said nucleic acid molecule is a plasmid.

3. The method of claim 2, wherein said differentiation antigen is a canine Her2/neu antigen, and wherein said xenogeneic antigen is a non-canine Her2/neu antigen.

4. The method of claim 3, wherein said xenogeneic Her2/neu antigen is a rat Her2/neu antigen.

5. The method of claim 4, wherein said plasmid comprises nucleotides 106-3882 of the sequence as set forth in SEQ ID NO: 1, or wherein said plasmid comprises nucleotides encoding the same peptide sequence as nucleotides 106-3882 of the sequence as set forth in SEQ ID NO: 1.

6. The method of claim 1, comprising the steps of:
    1) surgically debulking a canine mammary tumor/carcinoma expressing a Her2/neu differentiation antigen;
    2) administering a first nucleic acid molecule encoding a xenogeneic Her2/neu; and
    3) administering via electrotransfer/electroporation a second nucleic acid molecule; wherein the second nucleic acid molecule is either identical to said first nucleic acid molecule, or is a second, distinct nucleic acid molecule capable of expressing in vivo in a canine a different xenogeneic Her2/neu antigen, including those encoded by SEQ ID NOs:1, 3 or 4, or is a recombinant vector capable of expressing in vivo in said canine any Her2/neu protein, which is capable of eliciting a therapeutically effective immune response against heterologous Her2/neu expressed by said canine mammary tumor/carcinoma.

7. The method of claim 6, wherein the first nucleic acid molecule is a plasmid.

8. The method of claim 6, wherein:
1) the first administration consists of administering to said canine said first nucleic acid molecule without a needle;
2) the first nucleic acid molecule is capable of expressing in vivo in a canine a sequence comprising or consisting of the same sequence as set forth in SEQ ID NO:2; and
3) the second administration comprises or consists of administering said nucleic acid molecule of step 2.

9. The method of claim 8, wherein said first nucleic acid molecule is a plasmid.

10. The method of claim 6, wherein said second administration is provided to surviving canines once every about 3 to about 6 months.

11. The method of claim 8, wherein said second administration is provided to surviving canines once every about 3 to about 6 months.

12. The method of claim 1, which is performed about concurrently with resection of a mammary gland tumor (MGT).

13. The method of claim 4, which is performed about concurrently with resection of a mammary gland tumor (MGT).

14. The method of claim 1, wherein the administration is performed using a needle-free delivery device.

15. The method of claim 1, further comprising at least a second administration, provided at least once or at regular intervals after the initial antigen administration.

16. The method of claim 1, wherein:
a) the mean overall survival time is at least about 100 days greater;
b) the average disease-free survival time is at least about 200 days greater, and/or
c) the metastasis-free survival time is at least about 200 days greater in said canines receiving said nucleic acid molecule, relative to said canines receiving the surgical debulking without subsequent administration of said nucleic acid molecule.

17. The method of claim 16, wherein the three survival times are at least about 100, about 200, and about 200 days greater in the immunized canines relative to said canines receiving the surgical debulking without subsequent administration of said nucleic acid molecule, respectively.

18. The method of claim 9, wherein:
a) the mean overall survival time is at least about 100 days greater;
b) the average disease-free survival time is at least about 200 days greater, and/or
c) the metastasis-free survival time is at least about 200 days greater in said canines receiving said nucleic acid molecule, relative to said canines receiving the surgical debulking without subsequent administration of said first nucleic acid molecule.

19. The method of claim 18, wherein the three survival times are at least about 100, about 200, and about 200 days greater in the immunized canines relative to said canines receiving the surgical debulking without subsequent administration of said first nucleic acid molecule, respectively.

* * * * *

SEQUENCE LISTING

<160> NUMBER OF SEQ ID NOS: 4

<210> SEQ ID NO 1
<211> LENGTH: 4727
<212> TYPE: DNA
<213> ORGANISM: Rattus norvegicus

<400> SEQUENCE: 1

| | | | | | |
|---|---|---|---|---|---|
| gcgccccttc | ccaggcggcc | ccttccggcg | ccgcgcctgt | gcctgccctc | gccgcgcccc | 60 |
| gcgcccgcag | cctggtccag | cctgagccat | ggggccggag | ccgcaatgat | catcatggag | 120 |
| ctggcggcct | ggtgccgctg | ggggttcctc | ctcgccctcc | tgccccccgg | aatcgcgggc | 180 |
| acccaagtgt | gtaccggcac | agacatgaag | ttgcggctcc | ctgccagtcc | tgagacccac | 240 |
| ctggacatgc | tccgccacct | gtaccagggc | tgtcaggtag | tgcagggcaa | cttggagctt | 300 |
| acctacgtgc | ctgccaatgc | cagcctctca | ttcctgcagg | acatccagga | agttcagggt | 360 |
| tacatgctca | tcgctcacaa | ccaggtgaag | cgcgtcccac | tgcaaaggct | gcgcatcgtg | 420 |
| agagggaccc | agctctttga | ggacaagtat | gccctggctg | tgctagacaa | ccgagatcct | 480 |
| caggacaatg | tcgccgcctc | cacccccaggc | agaaccccag | aggggctgcg | ggagctgcag | 540 |
| cttcgaagtc | tcacagagat | cctgaaggga | ggagttttga | tccgtgggaa | ccctcagctc | 600 |
| tgctaccagg | acatggtttt | gtggaaggac | gtcttccgca | agaataacca | actggctcct | 660 |
| gtcgatatag | acaccaatcg | ttcccggggcc | tgtccacctt | gtgcccccgc | ctgcaaagac | 720 |
| aatcactgtt | ggggtgagag | tccggaagac | tgtcagatct | tgactggcac | catctgtacc | 780 |
| agtggttgtg | cccggtgcaa | gggccggctg | cccactgact | gctgccatga | gcagtgtgcc | 840 |
| gcaggctgca | cgggccccaa | gcattctgac | tgcctggcct | gcctccactt | caatcatagt | 900 |
| ggtatctgtg | agctgcactg | cccagccctc | gtcacctaca | acacagacac | ctttgagtcc | 960 |
| atgcacaacc | ctgagggtcg | ctacaccttt | ggtgccagct | gcgtgaccac | ctgcccctac | 1020 |
| aactacctgt | ctacggaagt | gggatcctgc | actctggtgt | gtccccgaa | taaccaagag | 1080 |
| gtcacagctg | aggacggaac | acagcgttgt | gagaaatgca | gcaagccctg | tgctcgagtg | 1140 |
| tgctatggtc | tgggcatgga | gcaccttcga | ggggcgaggg | ccatcaccag | tgacaatgtc | 1200 |
| caggagtttg | atggctgcaa | gaagatcttt | gggagcctgg | cattttttgcc | ggagagcttt | 1260 |
| gatggggacc | cctcctccgg | cattgctccg | ctgaggcctg | agcagctcca | agtgttcgaa | 1320 |
| accctggagg | agatcacagg | ttacctgtac | atctcagcat | ggccagacag | tctccgtgac | 1380 |
| ctcagtgtct | tccagaacct | tcgaatcatt | cggggacgga | ttctccacga | tggcgcgtac | 1440 |
| tcattgacac | tgcaaggcct | ggggatccac | tcgctgggc | tgcgctcact | gcgggagctg | 1500 |
| ggcagtggat | tggctctgat | tcaccgcaac | gcccatctct | gctttgtaca | cactgtacct | 1560 |
| tgggaccagc | tcttccggaa | cccacatcag | gccctgctcc | acagtgggaa | ccggccggaa | 1620 |
| gaggattgtg | gtctcgaggg | cttggtctgt | aactcactgt | gtgcccacgg | gcactgctgg | 1680 |
| gggccagggc | ccacccagtg | tgtcaactgc | agtcatttcc | ttcggggcca | ggagtgtgtg | 1740 |
| gaggagtgcc | gagtatggaa | ggggctcccc | cgggagtatg | tgagtgacaa | gcgctgtctg | 1800 |
| ccgtgtcacc | ccgagtgtca | gcctcaaaac | agctcagaga | cctgctttgg | atcggaggct | 1860 |
| gatcagtgtg | cagcctgcgc | ccactacaag | gactcgtcct | cctgtgtggc | tcgctgcccc | 1920 |
| agtggtgtga | aaccggacct | ctcctacatg | cccatctgga | gtacccgga | tgaggagggc | 1980 |
| atatgccagc | cgtgccccat | caactgcacc | cactcctgtg | tggatctgga | tgaacgaggc | 2040 |
| tgcccagcag | agcagagagc | cagcccggtg | acattcatca | ttgcaactgt | agtgggcgtc | 2100 |

-continued

```
ctgctgttcc tgatcttagt ggtggtcgtt ggaatcctaa tcaaacgaag gagacagaag    2160
atccggaagt atacgatgcg taggctgctg caggaaactg agttagtgga gccgctgacg    2220
cccagcggag caatgcccaa ccaggctcag atgcggatcc taaaagagac ggagctaagg    2280
aaggtgaagg tgcttggatc aggagctttt ggcactgtct acaagggcat ctggatccca    2340
gatggggaga atgtgaaaat ccccgtggct atcaaggtgt tgagagaaaa cacatctcct    2400
aaagccaaca aagaaattct agatgaagcg tatgtgatgg ctggtgtggg ttctccgtat    2460
gtgtcccgcc tcctgggcat ctgcctgaca tccacagtac agctggtgac acagcttatg    2520
ccctacggct gccttctgga ccatgtccga gaacaccgag gtcgcctagg ctcccaggac    2580
ctgctcaact ggtgtgttca gattgccaag gggatgagct acctggagga cgtgcggctt    2640
gtacacaggg acctggctgc ccggaatgtg ctagtcaaga gtcccaacca cgtcaagatt    2700
acagatttcg ggctggctcg gctgctggac attgatgaga cagagtacca tgcagatggg    2760
ggcaaggtgc ccatcaaatg gatggcattg gaatctattc tcagacgccg gttcacccat    2820
cagagtgatg tgtggagcta tggagtgact gtgtgggagc tgatgacttt tggggccaaa    2880
ccttacgatg gaatcccagc ccgggagatc cctgatttgc tggagaaggg agaacgccta    2940
cctcagcctc caatctgcac cattgatgtc tacatgatta tggtcaaatg ttggatgatt    3000
gactctgaat gtcgcccgag attccgggag ttggtgtcag aattttcacg tatggcgagg    3060 gaccccagc gttttgtggt catccagaac gaggacttgg gcccatccag ccccatggac    3120
agtaccttct accgttcact gctggaagat gatgacatgg gtgacctggt agacgctgaa    3180
gagtatctgg tgccccagca gggattcttc tccccggacc ctaccccagg cactgggagc    3240
acagcccata gaaggcaccg cagctcgtcc accaggagtg gaggtggtga gctgacactg    3300
ggcctggagc cctcggaaga agggccccc agatctccac tggctccctc ggaagggggct   3360 ggctccgatg tgtttgatgg tgacctggca atggggggtaa ccaaagggct gcagagcctc    3420
tctccacatg acctcagccc tctacagcgg tacagcgagg accccacatt acctctgccc    3480
cccgagactg atggctatgt tgctcccctg gcctgcagcc cccagcccga gtatgtgaac    3540
caatcagagg ttcagcctca gcctcccta acccagagg gtcctctgcc tcctgtccgg    3600
cctgctggtg ctactctaga aagacccaag actctctctc ctgggaagaa tggggttgtc    3660
aaagacgttt ttgccttcgg gggtgctgtg gagaaccctg aatacttagt accgagagaa    3720
ggcactgcct ctccgccca ccttctcct gccttcagcc cagcctttga caacctctat    3780
tactgggacc agaactcatc ggagcagggg cctccaccaa gtaactttga agggaccccc    3840
actgcagaga accctgagta cctaggcctg gatgtacctg tatgagacgt gtgcagacgt    3900
cctgtgcttt cagagtgggg aaggcctgac ttgtggtctc catcgccaca agcaggag    3960 agggtcctct ggccacatta catccagggc agacggctct accaggaacc tgccccgagg    4020 aaccttttcct tgctgcttga atcctgagtg gttaagaggg ccctgcctgg ctgggagaga    4080
tggcactgga cggcctctgg attacagacc ctgccctgac agactatagg gtccagtggg    4140
tatcatggcc atggcttctt gcctggcctg gctctcttgg ttctgaggac tgaggaaagc    4200
tcagcctaga agggaagagg tctggaggga acatcctggg aacaggacaa gcccactagga    4260 ctgagacaca tgcatcccaa cagggggctg cactttcatc cagaccagtc tttgtacaga    4320
gtgtattttg ttctgttttt acttttgctt ttttttttaa aaaagatga aataaggaca    4380 cggagggaga gtggatgtta gggaatggtg tccctctttc ttcatttaca atgagatttg    4440
```

```
taaaatagct gggccccagc ctatgcctgg gagtggtccc aggctagacc ttactgctca    4500
cctgacacac agctcctcct tgagttgagt gtgtagaagt tttccaaaag tttgagatgg    4560
tttggctttg gggttgaggg actgggaagt taggatcctt tctgagggcc ctttggcaac    4620
aggatcattc ttcattggac gcactcattc caaggctacc cctagaatga agtccttccc    4680
tcccagtggg agagtggccc ttgaaaggag cactgtcaca tgactca                  4727
```

<210> SEQ ID NO 2
<211> LENGTH: 1259
<212> TYPE: PRT
<213> ORGANISM: Rattus norvegicus

<400> SEQUENCE: 2

```
Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
            20                  25                  30

Asp Met Lys Leu Arg Leu Pro Ala Ser Pro Glu Thr His Leu Asp Met
        35                  40                  45

Leu Arg His Leu Tyr Gln Gly Cys Gln Val Val Gln Gly Asn Leu Glu
    50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
        115                 120                 125

Val Ala Ala Ser Thr Pro Gly Arg Thr Pro Glu Gly Leu Arg Glu Leu
    130                 135                 140

Gln Leu Arg Ser Leu Thr Glu Ile Leu Lys Gly Gly Val Leu Ile Arg
145                 150                 155                 160

Gly Asn Pro Gln Leu Cys Tyr Gln Asp Met Val Leu Trp Lys Asp Val
                165                 170                 175

Phe Arg Lys Asn Asn Gln Leu Ala Pro Val Asp Ile Asp Thr Asn Arg
            180                 185                 190

Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
                245                 250                 255

Leu Ala Cys Leu His Phe Asn His Ser Gly Ile Cys Glu Leu His Cys
            260                 265                 270

Pro Ala Leu Val Thr Tyr Asn Thr Asp Thr Phe Glu Ser Met His Asn
        275                 280                 285

Pro Glu Gly Arg Tyr Thr Phe Gly Ala Ser Cys Val Thr Thr Cys Pro
    290                 295                 300

Tyr Asn Tyr Leu Ser Thr Glu Val Gly Ser Cys Thr Leu Val Cys Pro
305                 310                 315                 320

Pro Asn Asn Gln Glu Val Thr Ala Glu Asp Gly Thr Gln Arg Cys Glu
```

-continued

```
                325                 330                 335
Lys Cys Ser Lys Pro Cys Ala Arg Val Cys Tyr Gly Leu Gly Met Glu
            340                 345                 350
His Leu Arg Gly Ala Arg Ala Ile Thr Ser Asp Asn Val Gln Glu Phe
            355                 360                 365
Asp Gly Cys Lys Lys Ile Phe Gly Ser Leu Ala Phe Leu Pro Glu Ser
            370                 375                 380
Phe Asp Gly Asp Pro Ser Ser Gly Ile Ala Pro Leu Arg Pro Glu Gln
385                 390                 395                 400
Leu Gln Val Phe Glu Thr Leu Glu Glu Ile Thr Gly Tyr Leu Tyr Ile
                405                 410                 415
Ser Ala Trp Pro Asp Ser Leu Arg Asp Leu Ser Val Phe Gln Asn Leu
            420                 425                 430
Arg Ile Ile Arg Gly Arg Ile Leu His Asp Gly Ala Tyr Ser Leu Thr
            435                 440                 445
Leu Gln Gly Leu Gly Ile His Ser Leu Gly Leu Arg Ser Leu Arg Glu
            450                 455                 460
Leu Gly Ser Gly Leu Ala Leu Ile His Arg Asn Ala His Leu Cys Phe
465                 470                 475                 480
Val His Thr Val Pro Trp Asp Gln Leu Phe Arg Asn Pro His Gln Ala
                485                 490                 495
Leu Leu His Ser Gly Asn Arg Pro Glu Glu Asp Cys Gly Leu Glu Gly
            500                 505                 510
Leu Val Cys Asn Ser Leu Cys Ala His Gly His Cys Trp Gly Pro Gly
            515                 520                 525
Pro Thr Gln Cys Val Asn Cys Ser His Phe Leu Arg Gly Gln Glu Cys
            530                 535                 540
Val Glu Glu Cys Arg Val Trp Lys Gly Leu Pro Arg Glu Tyr Val Ser
545                 550                 555                 560
Asp Lys Arg Cys Leu Pro Cys His Pro Glu Cys Gln Pro Gln Asn Ser
                565                 570                 575
Ser Glu Thr Cys Phe Gly Ser Glu Ala Asp Gln Cys Ala Ala Cys Ala
            580                 585                 590
His Tyr Lys Asp Ser Ser Ser Cys Val Ala Arg Cys Pro Ser Gly Val
            595                 600                 605
Lys Pro Asp Leu Ser Tyr Met Pro Ile Trp Lys Tyr Pro Asp Glu Glu
            610                 615                 620
Gly Ile Cys Gln Pro Cys Pro Ile Asn Cys Thr His Ser Cys Val Asp
625                 630                 635                 640
Leu Asp Glu Arg Gly Cys Pro Ala Glu Gln Arg Ala Ser Pro Val Thr
                645                 650                 655
Phe Ile Ile Ala Thr Val Val Gly Val Leu Leu Phe Leu Ile Leu Val
            660                 665                 670
Val Val Val Gly Ile Leu Ile Lys Arg Arg Arg Gln Lys Ile Arg Lys
            675                 680                 685
Tyr Thr Met Arg Arg Leu Leu Gln Glu Thr Glu Leu Val Glu Pro Leu
            690                 695                 700
Thr Pro Ser Gly Ala Met Pro Asn Gln Ala Gln Met Arg Ile Leu Lys
705                 710                 715                 720
Glu Thr Glu Leu Arg Lys Val Lys Val Leu Gly Ser Gly Ala Phe Gly
                725                 730                 735
Thr Val Tyr Lys Gly Ile Trp Ile Pro Asp Gly Glu Asn Val Lys Ile
            740                 745                 750
```

-continued

Pro Val Ala Ile Lys Val Leu Arg Glu Asn Thr Ser Pro Lys Ala Asn
    755                 760                 765

Lys Glu Ile Leu Asp Glu Ala Tyr Val Met Ala Gly Val Gly Ser Pro
770                 775                 780

Tyr Val Ser Arg Leu Leu Gly Ile Cys Leu Thr Ser Thr Val Gln Leu
785                 790                 795                 800

Val Thr Gln Leu Met Pro Tyr Gly Cys Leu Leu Asp His Val Arg Glu
                805                 810                 815

His Arg Gly Arg Leu Gly Ser Gln Asp Leu Leu Asn Trp Cys Val Gln
                820                 825                 830

Ile Ala Lys Gly Met Ser Tyr Leu Glu Asp Val Arg Leu Val His Arg
                835                 840                 845

Asp Leu Ala Ala Arg Asn Val Leu Val Lys Ser Pro Asn His Val Lys
850                 855                 860

Ile Thr Asp Phe Gly Leu Ala Arg Leu Leu Asp Ile Asp Glu Thr Glu
865                 870                 875                 880

Tyr His Ala Asp Gly Gly Lys Val Pro Ile Lys Trp Met Ala Leu Glu
                885                 890                 895

Ser Ile Leu Arg Arg Arg Phe Thr His Gln Ser Asp Val Trp Ser Tyr
                900                 905                 910

Gly Val Thr Val Trp Glu Leu Met Thr Phe Gly Ala Lys Pro Tyr Asp
                915                 920                 925

Gly Ile Pro Ala Arg Glu Ile Pro Asp Leu Leu Glu Lys Gly Glu Arg
                930                 935                 940

Leu Pro Gln Pro Pro Ile Cys Thr Ile Asp Val Tyr Met Ile Met Val
945                 950                 955                 960

Lys Cys Trp Met Ile Asp Ser Glu Cys Arg Pro Arg Phe Arg Glu Leu
                965                 970                 975

Val Ser Glu Phe Ser Arg Met Ala Arg Asp Pro Gln Arg Phe Val Val
                980                 985                 990

Ile Gln Asn Glu Asp Leu Gly Pro Ser Ser Pro Met Asp Ser Thr Phe
                995                 1000                1005

Tyr Arg Ser Leu Leu Glu Asp Asp Met Gly Asp Leu Val Asp
    1010                1015                1020

Ala Glu Glu Tyr Leu Val Pro Gln Gln Gly Phe Phe Ser Pro Asp
    1025                1030                1035

Pro Thr Pro Gly Thr Gly Ser Thr Ala His Arg Arg His Arg Ser
    1040                1045                1050

Ser Ser Thr Arg Ser Gly Gly Gly Glu Leu Thr Leu Gly Leu Glu
    1055                1060                1065

Pro Ser Glu Glu Gly Pro Pro Arg Ser Pro Leu Ala Pro Ser Glu
    1070                1075                1080

Gly Ala Gly Ser Asp Val Phe Asp Gly Asp Leu Ala Met Gly Val
    1085                1090                1095

Thr Lys Gly Leu Gln Ser Leu Ser Pro His Asp Leu Ser Pro Leu
    1100                1105                1110

Gln Arg Tyr Ser Glu Asp Pro Thr Leu Pro Leu Pro Pro Glu Thr
    1115                1120                1125

Asp Gly Tyr Val Ala Pro Leu Ala Cys Ser Pro Gln Pro Glu Tyr
    1130                1135                1140

Val Asn Gln Ser Glu Val Gln Pro Gln Pro Pro Leu Thr Pro Glu
    1145                1150                1155

| Gly | Pro | Leu | Pro | Pro | Val | Arg | Pro | Ala | Gly | Ala | Thr | Leu | Glu | Arg |
|---|---|---|---|---|---|---|---|---|---|---|---|---|---|---|
| 1160 | | | | | 1165 | | | | | 1170 | | | | |

| Pro | Lys | Thr | Leu | Ser | Pro | Gly | Lys | Asn | Gly | Val | Val | Lys | Asp | Val |
|---|---|---|---|---|---|---|---|---|---|---|---|---|---|---|
| 1175 | | | | | 1180 | | | | | 1185 | | | | |

| Phe | Ala | Phe | Gly | Gly | Ala | Val | Glu | Asn | Pro | Glu | Tyr | Leu | Val | Pro |
|---|---|---|---|---|---|---|---|---|---|---|---|---|---|---|
| 1190 | | | | | 1195 | | | | | 1200 | | | | |

| Arg | Glu | Gly | Thr | Ala | Ser | Pro | Pro | His | Pro | Ser | Pro | Ala | Phe | Ser |
|---|---|---|---|---|---|---|---|---|---|---|---|---|---|---|
| 1205 | | | | | 1210 | | | | | 1215 | | | | |

| Pro | Ala | Phe | Asp | Asn | Leu | Tyr | Tyr | Trp | Asp | Gln | Asn | Ser | Ser | Glu |
|---|---|---|---|---|---|---|---|---|---|---|---|---|---|---|
| 1220 | | | | | 1225 | | | | | 1230 | | | | |

| Gln | Gly | Pro | Pro | Pro | Ser | Asn | Phe | Glu | Gly | Thr | Pro | Thr | Ala | Glu |
|---|---|---|---|---|---|---|---|---|---|---|---|---|---|---|
| 1235 | | | | | 1240 | | | | | 1245 | | | | |

| Asn | Pro | Glu | Tyr | Leu | Gly | Leu | Asp | Val | Pro | Val |
|---|---|---|---|---|---|---|---|---|---|---|
| 1250 | | | | | 1255 | | | | | |

<210> SEQ ID NO 3
<211> LENGTH: 3768
<212> TYPE: DNA
<213> ORGANISM: Mus musculus

<400> SEQUENCE: 3

| | | | | | |
|---|---|---|---|---|---|
| atggagctgg | cggcctggtg | ccgttggggg | ttcctcctcg | ccctcctgtc | cccggagcc | 60 |
| gcgggtaccc | aagtgtgtac | cggtaccgac | atgaagttgc | gactccctgc | cagtcctgag | 120 |
| acccacctgg | acatgcttcg | ccacctctac | cagggctgtc | aggtggtgca | gggcaatttg | 180 |
| gagcttacct | acctgcccgc | caatgccagc | ctctcattcc | tgcaggacat | ccaggaagtc | 240 |
| cagggataca | tgctcatcgc | tcacaaccga | gtgaaacacg | tcccactgca | gaggttgcgc | 300 |
| atcgtgagag | ggactcagct | cttttgaggac | aagtatgccc | tggctgtgct | agacaaccga | 360 |
| gacccttttgg | acaacgtcac | caccgccgcc | ccaggcagaa | cccagaagg | gctgcgggag | 420 |
| ctgcagcttc | gaagtctcac | agagatcttg | aagggaggag | ttttgatccg | tgggaaccct | 480 |
| cagctctgct | accaggacat | ggttttgtgg | aaggatgtcc | tccgtaagaa | taaccagctg | 540 |
| gctcctgtcg | acatggacac | caatcgttcc | cgggcctgtc | caccttgtgc | cccaacctgc | 600 |
| aaagacaatc | actgttgggg | tgagagtcct | gaagactgtc | agatcttgac | tggcaccatc | 660 |
| tgtactagtg | gctgtgcccg | gtgcaagggc | cggctgccca | ctgactgttg | ccatgagcag | 720 |
| tgtgctgcag | gctgcacggg | tcccaagcat | tctgactgcc | tggcctgcct | ccacttcaat | 780 |
| catagtggta | tctgtgagct | gcactgcccg | gccctcatca | cctacaacac | agacaccttc | 840 |
| gagtccatgc | tcaaccctga | gggtcgctac | acctttggtg | ccagctgtgt | gaccacctgc | 900 |
| ccctacaact | acctctccac | ggaagtggga | tcctgcactc | tggtctgtcc | cccgaacaac | 960 |
| caagaggtca | gagctgagga | cggaacacag | cggtgtgaga | aatgcagcaa | gccctgtgct | 1020 |
| ggagtatgct | atggtctggg | catggagcac | ctccgagggg | cgagggccat | caccagtgac | 1080 |
| aatatccagg | agtttgctgg | ctgcaagaag | atctttggga | gcctggcatt | tttgccggag | 1140 |
| agctttgatg | gaaccccctc | ctccggcgtt | gccccactga | agccagagca | tctccaagtg | 1200 |
| ttcgaaaccc | tggaggagat | cacaggttac | ctatacattt | cagcatggcc | agagagcttc | 1260 |
| caagacctca | gtgtcttcca | gaaccttcgg | gtcattcggg | gacggattct | ccatgatggt | 1320 |
| gcttactcat | tgacgttgca | aggcctgggg | attcactcac | tggggctacg | ctcactgcgg | 1380 |
| gagctgggca | gtggattggc | tctcattcac | cgcaacaccc | atctctgctt | tgtaaacact | 1440 |
| gtaccttggg | accagctctt | ccggaacccg | caccaggccc | tactccacag | tgggaaccgg | 1500 |

-continued

```
ccagaagagg catgtggtct tgagggcttg gtctgtaact cactgtgtgc ccgtgggcac    1560
tgctgggggc cagggcccac ccagtgtgtc aactgcagtc agttcctccg gggccaggag    1620
tgtgtggagg agtgccgagt atggaagggg ctccccaggg agtatgtgag gggcaagcac    1680
tgtctgccat gccaccccga gtgtcagcct caaaacagct cggagacctg ctatggatcg    1740
gaggctgacc agtgtgaggc ttgtgcccac tacaaggact catcttcctg tgtggctcgc    1800
tgccccagtg gtgtgaagcc agacctctcc tacatgccta tctggaagta cccggatgag    1860
gagggcatat gtcagccatg ccccatcaac tgcacccact catgtgtgga cctggacgaa    1920
cgaggctgcc cagcagagca gagagccagc ccagtgacat tcatcattgc aactgtggtg    1980
ggcgtcctgt tgttcctgat catagtggtg gtcattggaa tcctaatcaa cgaaggcga    2040
cagaagatcc ggaagtatac catgcgtagg ctgctgcagg agaccgagct ggtggagccg    2100
ctgacgccca gtggagctgt gcccaaccag gctcagatgc ggatcctaaa ggagacagag    2160
ctaaggaagc tgaaggtgct tgggtcagga gccttcggca ctgtctacaa gggcatctgg    2220
atcccagatg gggagaacgt gaaaatcccc gtggccatca aggtgttgag ggaaaacaca    2280
tctcctaaag ctaacaaaga aatcctagat gaagcgtacg tcatggctgg tgtgggttct    2340
ccatatgtgt cccgcctcct gggcatctgc ctgacatcca cagtgcagct ggtgacacag    2400
cttatgccct atggctgcct tctggaccat gtccgagaac accgaggtcg cttaggctcc    2460
caggacctgc tcaactggtg tgttcagatt gccaagggga tgagctacct ggaggaagtt    2520
cggcttgttc acagggacct agctgcccga aacgtgctag tcaagagtcc caaccacgtc    2580
aagattaccg acttcgggct ggcacggctg ctggacattg atgagactga ataccatgca    2640
gatgggggca aggtgcccat caagtggatg gcattggaat ctattctcag acgccggttc    2700
acccatcaga gtgatgtgtg gagctatggt gtgactgtgt gggagctgat gacctttggg    2760
gccaaacctt acgatgggat cccagctcgg gagatccctg atttgctgga agggagaa    2820
cgcctacctc agcctccaat ctgcaccatc gacgtctaca tgatcatggt caaatgttgg    2880
atgattgact ccgaatgtcg cccgagattc cgggagttgg tatcagaatt ctcccgtatg    2940
gcaagggacc cccagcgctt tgtggtcatc cagaacgagg acttaggccc ctccagcccc    3000
atggacagca ccttctaccg ttcactgctg gaggatgatg acatggggga gctggtcgat    3060
gctgaagagt acctggtacc ccagcaggga ttcttctccc cagaccctgc cctaggtact    3120
gggagcacag cccaccgcag acaccgcagc tcgtcggcca ggagtggcgg tggtgagctg    3180
acactgggcc tggagccctc ggaagaagag ccccccagat ctccactggc tccctccgaa    3240
ggggctggct ccgatgtgtt tgatggtgac ctggcagtgg gggtaaccaa aggactgcag    3300
agcctctctc cacatgacct cagccctcta cagcggtaca gtgaggatcc cacattacct    3360
ctgcccccg agactgatgg ctacgttgct cccctggcct gcagccccca gcccgagtat    3420
gtgaaccagc cagaggttcg gcctcagtct cccttgaccc cagagggtcc tccgcctccc    3480
atccgacctg ctggtgctac tctagaaaga cccaagactc tctctcctgg gaaaaatggg    3540
gttgtcaaag acgttttttgc ctttgggggt gctgtggaga accctgaata cttagcaccc    3600
agagcaggca ctgcctctca gccccaccct tctcctgcct tcagcccagc ctttgacaac    3660
ctctattact gggaccagaa ctcatcggag cagggtcctc caccaagtac ctttgaaggg    3720
accccccactg cagagaaccc tgagtaccta ggcctggatg tgccagta              3768
```

<210> SEQ ID NO 4
<211> LENGTH: 3765

<212> TYPE: DNA
<213> ORGANISM: homo sapiens

<400> SEQUENCE: 4

| | | | | | |
|---|---|---|---|---|---|
| atggagctgg | cggccttgtg | ccgctggggg | ctcctcctcg | ccctcttgcc | ccccggagcc | 60 |
| gcgagcaccc | aagtgtgcac | cggcacagac | atgaagctgc | ggctccctgc | cagtcccgag | 120 |
| acccacctgg | acatgctccg | ccacctctac | cagggctgcc | aggtggtgca | gggaaacctg | 180 |
| gaactcacct | acctgcccac | caatgccagc | ctgtccttcc | tgcaggatat | ccaggaggtg | 240 |
| cagggctacg | tgctcatcgc | tcacaaccaa | gtgaggcagg | tcccactgca | gaggctgcgg | 300 |
| attgtgcgag | gcacccagct | ctttgaggac | aactatgccc | tggccgtgct | agacaatgga | 360 |
| gacccgctga | caataccacc | ccctgtcaca | ggggcctccc | caggaggcct | gcgggagctg | 420 |
| cagcttcgaa | gcctcacaga | gatcttgaaa | ggaggggtct | tgatccagcg | gaaccccag | 480 |
| ctctgctacc | aggacacgat | tttgtggaag | acatcttcc | acaagaacaa | ccagctggct | 540 |
| ctcacactga | tagacaccaa | ccgctctcgg | gcctgccacc | cctgttctcc | gatgtgtaag | 600 |
| ggctcccgct | gctggggaga | gagttctgag | gattgtcaga | gcctgacgcg | cactgtctgt | 660 |
| gccggtggct | gtgcccgctg | caaggggcca | ctgcccactg | actgctgcca | tgagcagtgt | 720 |
| gctgccggct | gcacgggccc | caagcactct | gactgcctgg | cctgcctcca | cttcaaccac | 780 |
| agtggcatct | gtgagctgca | ctgcccagcc | ctggtcacct | acaacacaga | cacgtttgag | 840 |
| tccatgccca | atcccgaggg | ccggtataca | ttcggcgcca | gctgtgtgac | tgcctgtccc | 900 |
| tacaactacc | tttctacgga | cgtgggatcc | tgcaccctcg | tctgccccct | gcacaaccaa | 960 |
| gaggtgacag | cagaggatgg | aacacagcgg | tgtgagaagt | gcagcaagcc | ctgtgcccga | 1020 |
| gtgtgctatg | gtctgggcat | ggagcacttg | cgagaggtga | gggcagttac | cagtgccaat | 1080 |
| atccaggagt | ttgctggctg | caagaagatc | tttgggagcc | tggcatttct | gccggagagc | 1140 |
| tttgatgggg | acccagcctc | caacactgcc | ccgctccagc | cagagcagct | ccaagtgttt | 1200 |
| gagactctgg | aagagatcac | aggttaccta | tacatctcag | catggccgga | cagcctgcct | 1260 |
| gacctcagcg | tcttccagaa | cctgcaagta | atccggggac | gaattctgca | caatggcgcc | 1320 |
| tactcgctga | ccctgcaagg | gctgggcatc | agctggctgg | gctgcgctc | actgagggaa | 1380 |
| ctgggcagtg | gactgccct | catccaccat | aacacccacc | tctgcttcgt | gcacacggtg | 1440 |
| ccctgggacc | agctctttcg | gaacccgcac | caagctctgc | tccacactgc | caaccggcca | 1500 |
| gaggacgagt | gtgtgggcga | gggcctggcc | tgccaccagc | tgtgcgcccg | agggcactgc | 1560 |
| tggggtccag | ggcccaccca | gtgtgtcaac | tgcagccagt | tccttcgggg | ccaggagtgc | 1620 |
| gtggaggaat | gccgagtact | gcaggggctc | cccagggagt | atgtgaatgc | caggcactgt | 1680 |
| ttgccgtgcc | accctgagtg | tcagccccag | aatggctcag | tgacctgttt | tggaccggag | 1740 |
| gctgaccagt | gtgtggcctg | tgcccactat | aaggaccctc | ccttctgcgt | ggcccgctgc | 1800 |
| cccagcggtg | tgaaacctga | cctctcctac | atgcccatct | ggaagtttcc | agatgaggag | 1860 |
| ggcgcatgcc | agccttgccc | catcaactgc | acccactcct | gtgtggacct | ggatgacaag | 1920 |
| ggctgccccg | ccgagcagag | agccagccct | ctgacgtcca | tcatctctgc | ggtggttggc | 1980 |
| attctgctgg | tcgtggtctt | gggggtggtc | tttgggatcc | tcatcaagcg | acggcagcag | 2040 |
| aagatccgga | agtacacgat | gcggagactg | ctgcaggaaa | cggagctggt | ggagccgctg | 2100 |
| acacctagcg | gagcgatgcc | caaccaggcg | cagatgcgga | tcctgaaaga | gacggagctg | 2160 |
| aggaaggtga | aggtgcttgg | atctggcgct | tttggcacag | tctacaaggg | catctggatc | 2220 |

```
cctgatgggg agaatgtgaa aattccagtg gccatcaaag tgttgaggga aaacacatcc    2280
cccaaagcca acaaagaaat cttagacgaa gcatacgtga tggctggtgt gggctcccca    2340
tatgtctccc gccttctggg catctgcctg acatccacgg tgcagctggt gacacagctt    2400
atgccctatg gctgcctctt agaccatgtc cgggaaaacc gcggacgcct gggctcccag    2460
gacctgctga actggtgtat gcagattgcc aagggatga gctacctgga ggatgtgcgg     2520
ctcgtacaca gggacttggc cgctcggaac gtgctggtca agagtcccaa ccatgtcaaa    2580
attacagact tcgggctggc tcggctgctg gacattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccggag atccctgacc tgctggaaaa ggggagcgg     2820 ctgccccagc cccccatctg caccattgat gtctacatga tcatggtcaa atgttggatg    2880
attgactctg aatgtcggcc aagattccgg gagttggtgt ctgaattctc ccgcatggcc    2940
agggaccccc agcgctttgt ggtcatccag aatgaggact gggcccagc cagtcccttg     3000 gacagcacct tctaccgctc actgctggag gacgatgaca tggggacct ggtggatgct     3060 gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgaccccag ccctctacag cggtacagtg aggacccac agtaccctg      3360 ccctctgaga ctgatggcta cgttgccccc ctgacctgca gccccagcc tgaatatgtg     3420 aaccagccag atgttcggcc ccagccccct tcgccccgag agggccctct gcctgctgcc    3480
cgacctgctg gtgccactct ggaaaggccc aagactctct ccccagggaa gaatggggtc    3540
gtcaaagacg tttttgcctt tgggggtgcc gtggagaacc ccgagtactt gacacccag     3600 ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtg                    3765
```